United States Patent [19]

McEwen et al.

[11] Patent Number: 4,828,716
[45] Date of Patent: May 9, 1989

[54] APPARATUS AND METHOD FOR SEPARATING PHASES OF BLOOD

[75] Inventors: James A. McEwen, Richmond; William J. Godolphin, Vancouver; Rainer M. Bohl, Vancouver; Mark N. Dance, Vancouver; Martin L. Furse, Vancouver; John C. Osborne, Vancouver, all of Canada

[73] Assignee: Andronic Devices, Ltd., Vancouver, Canada

[21] Appl. No.: 33,769

[22] Filed: Apr. 3, 1987

[51] Int. Cl.[4] .......................... B01D 33/02; B04B 1/06
[52] U.S. Cl. ..................................... 210/740; 210/744; 210/745; 210/782; 210/789; 210/104; 210/143; 422/72; 422/102; 436/177; 494/7; 494/10; 494/19; 494/37
[58] Field of Search .................... 494/7, 10, 11, 19, 37; 210/104, 143, 516, 518, 739, 740, 744, 745, 782, 789, 512.1, 787; 422/102, 72; 436/177

[56] References Cited

U.S. PATENT DOCUMENTS

| | | | |
|---|---|---|---|
| 2,460,641 | 2/1949 | Kleiner | 128/769 |
| 3,468,474 | 9/1969 | Shoblom et al. | 233/27 |
| 3,508,653 | 4/1970 | Coleman | 210/516 |
| 3,741,400 | 6/1973 | Dick | 210/516 |
| 3,813,031 | 5/1974 | Anderson | 233/26 |
| 3,849,072 | 11/1974 | Ayres | 23/259 |
| 3,852,194 | 12/1974 | Zine, Jr. | 210/789 |
| 3,929,646 | 12/1975 | Adler | 210/789 |
| 3,957,197 | 5/1976 | Sartory et al. | 233/4 |
| 3,957,654 | 5/1976 | Ayres | 210/516 |
| 4,021,352 | 5/1977 | Sarstedt | 210/789 X |
| 4,046,699 | 9/1977 | Zine, Jr. | 210/516 |
| 4,083,784 | 4/1978 | Zine, Jr. | 210/789 |
| 4,152,270 | 5/1979 | Ballies | 210/516 |
| 4,189,382 | 2/1980 | Zine, Jr. | 210/714 |
| 4,202,769 | 5/1980 | Greenspan | 210/789 |
| 4,278,202 | 7/1981 | Westberg | 233/27 |
| 4,279,863 | 7/1981 | Friehler | 422/102 |
| 4,283,276 | 8/1981 | Grant | 209/155 |
| 4,284,602 | 8/1981 | Kelton et al. | 422/72 |
| 4,285,810 | 8/1981 | Kirkland et al. | 209/155 |
| 4,322,298 | 3/1982 | Porsidsky | 210/787 |
| 4,326,959 | 4/1982 | Ferrars | 210/516 |
| 4,350,593 | 9/1982 | Kessler | 210/516 |
| 4,369,117 | 1/1983 | White | 210/782 |
| 4,417,981 | 11/1983 | Nugent et al. | 210/209 |
| 4,425,235 | 1/1984 | Cornell et al. | 210/516 |
| 4,443,345 | 4/1984 | Wells | 210/782 |
| 4,446,106 | 5/1984 | Nelson et al. | 422/72 |
| 4,447,220 | 5/1984 | Eberle | 494/26 |
| 4,451,250 | 5/1984 | Romanauskas | 494/85 |
| 4,464,254 | 8/1984 | Dojki et al. | 210/516 |
| 4,492,634 | 1/1985 | Villa-Real | 210/516 |
| 4,522,713 | 6/1985 | Nussbaumer et al. | 210/136 |
| 4,530,691 | 7/1985 | Brown | 210/787 X |
| 4,534,465 | 8/1985 | Rothermel et al. | 422/104 X |
| 4,550,084 | 10/1985 | Nelson et al. | 436/45 |
| 4,602,995 | 7/1986 | Cassaday et al. | 210/516 |
| 4,639,316 | 1/1987 | Eldegheidy | 210/416.1 |

OTHER PUBLICATIONS 10 page instruction manual on the Beckman Airfuge Ultracentrifuge AF-IM-5.
21-page article on Preparative Zonal Centrifugation in Methods of Biochemical Analysis, vol. XV.
3 page brochure of Sarstedt showing Monovette and Safety Monovette Beckman 3-page brochure of Jun. 1981.
1 page brochure introducing Stat-Spin Technology.

Primary Examiner—Richard V. Fisher
Assistant Examiner—W. Gary Jones
Attorney, Agent, or Firm—Stoel Rives Boley Jones & Grey

[57] ABSTRACT

Method and apparatus for partitioning a pre-selected phase of a sample of liquid, such as blood, having a plurality of phases of differing densities the method comprising the steps of introducing a sample into a chamber of constant cross-sectional shape and a volume greater than that of the sample, ordering the phases of the sample concentrically by rotating the chamber about its longitudinal axis, reducing the volume of the chamber in response to a separation control signal, removing a portion of the separated sample in order of phase, deriving information about the portion of the sample being removed from the chamber and modifying the separation control signal in response to the derived information. Also disclosed is an apparatus for separating a pre-selected phase of a sample contained in an enclosed chamber, wherein said apparatus can be used with a separating means which rotates the chamber about either a longitudinal axis of the chamber, or about an axis perpendicular to the longitudinal axis of the chamber and not passing through the chamber. In addition, separating means in which such an enclosed chamber is rotated about a longitudinal axis is described.

9 Claims, 7 Drawing Sheets

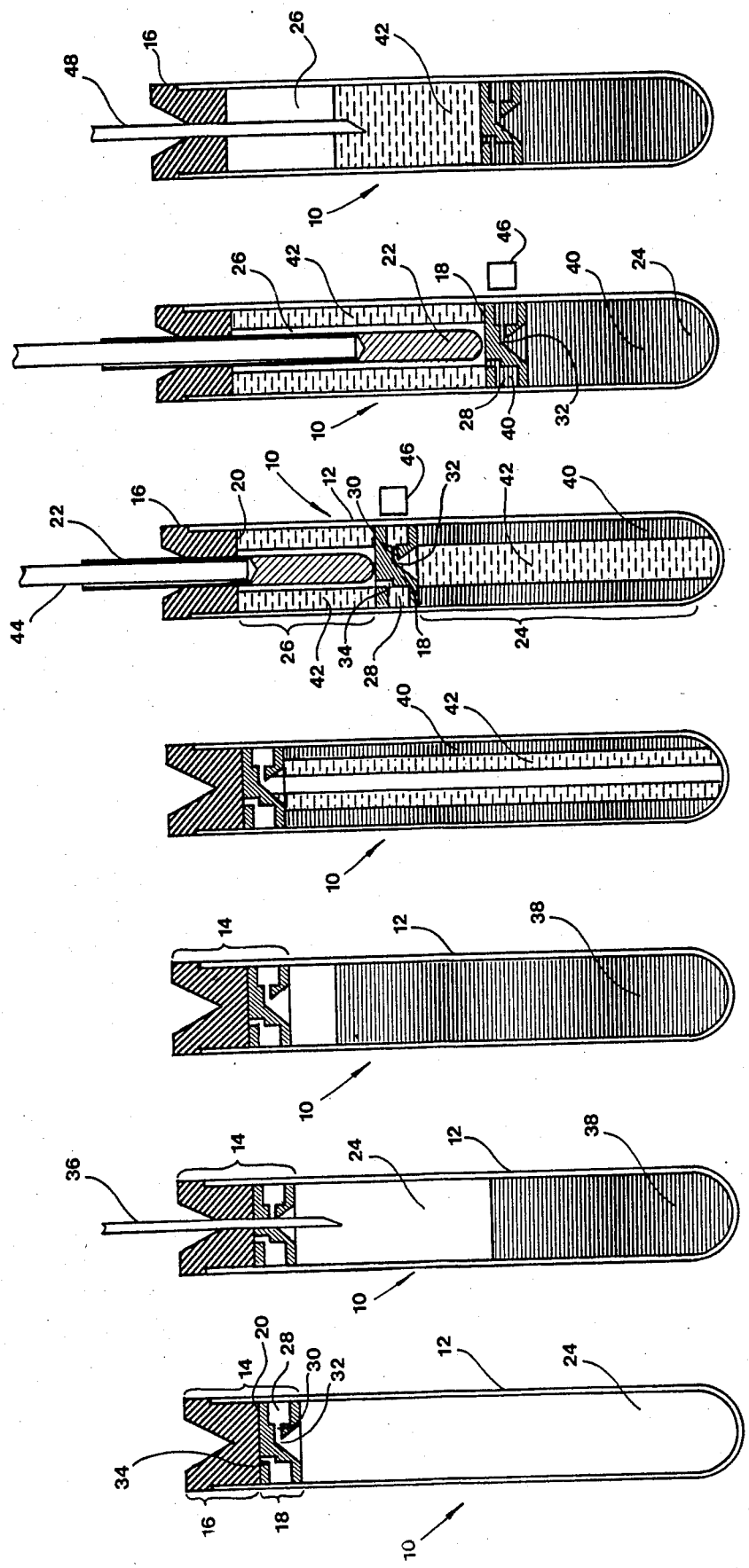

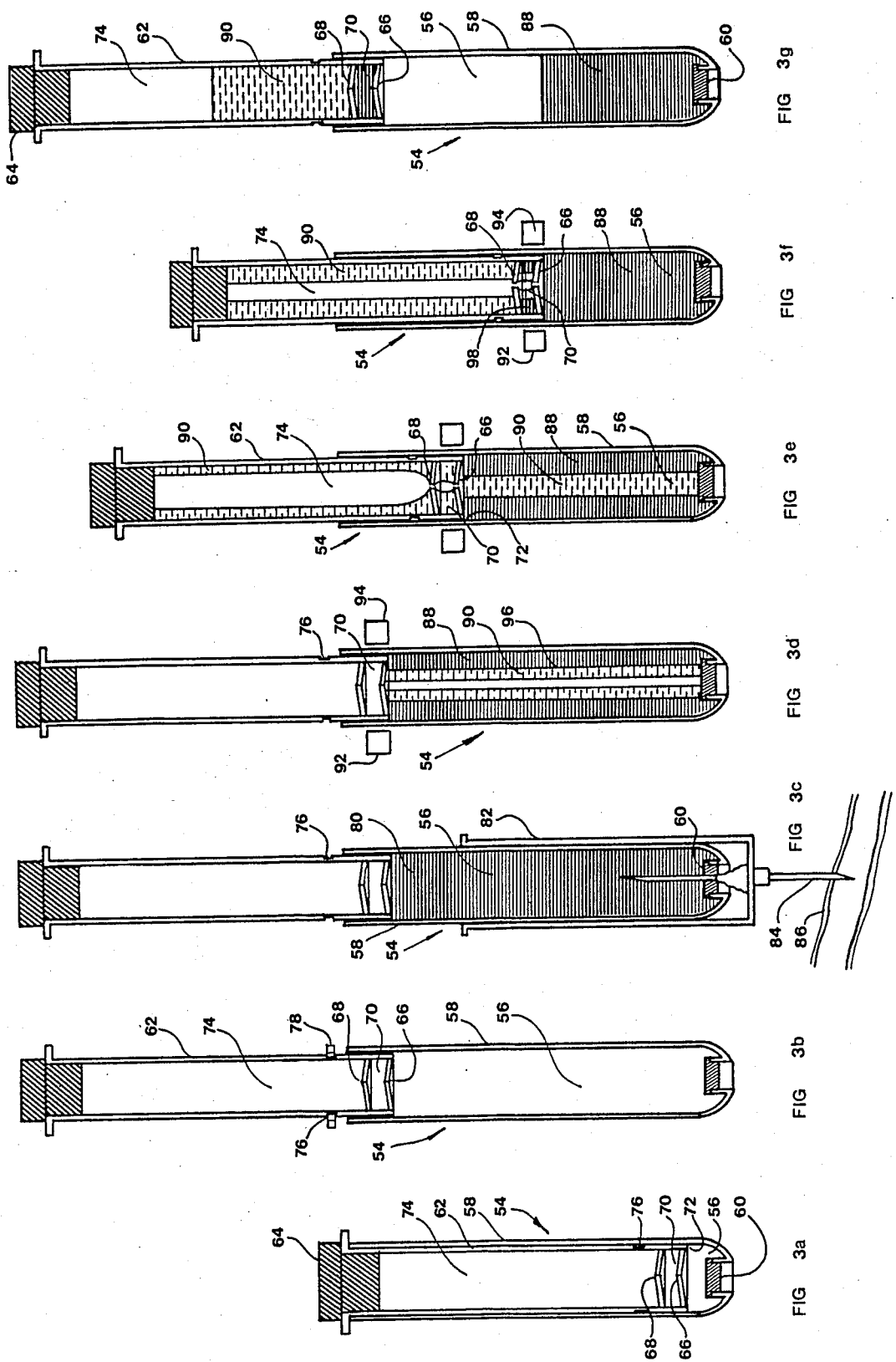

APPARATUS AND METHOD FOR SEPARATING PHASES OF BLOOD

FIELD OF THE INVENTION

The present invention refers to a method and apparatus for separating a pre-selected phase of a sample of liquid such as blood contained in a chamber, and pertains to means for ordering the phases of a sample of liquid contained in a chamber by rotating the chamber about its longitudinal axis. In particular, the invention pertains to apparatus for collecting a blood sample in a test tube or syringe-like device, separating the phases of the blood sample by rotating the test tube or syringe like device about a longitudinal axis, and receiving from the device the separated phases in order of phase.

BACKGROUND OF THE INVENTION

Blood to be analyzed for diagnostic and monitoring purposes is customarily collected by venipuncture through a special cannula or needle attached to a syringe or evacuated collection tube. Such collection techniques and devices must offer ease and flexibility of use because of the large number of blood specimens that are processed and because of requirements for additives, variable volumes and adaptation to individual medical conditions.

Separation of the constituent phases, serum or plasma from the cells, is often necessary for laboratory analysis and is usually carried out by centrifugation or, occasionally, by filtration. This separation may require fractionation of minor as well as major components. Once separated the phases are best kept in an inert container, physically and chemically isolated, to avoid disturbance of analyte concentrations. It may be necessary to store them under controlled environmental conditions of temperature, atmosphere or light.

The blood and its fractions have characteristics of volume, color and turbidity, of which it is important the analyst take note, since these may affect subsequent analyses. The blood may contain infectious agents and should be kept isolated, preferably in a closed system to reduce exposure to laboratory personnel. Blood specimens may be processed in small numbers in physicians' offices where compactness and simplicity of use are required or in large numbers in clinics and hospitals where efficiency and assured identification are essential and automation is desirable.

Thus there is a need for a blood collection and separation device or system which combines the features of: ability to separate the blood phases under conditions which limit personnel exposure; maintenance of these phases separated and unchanged; monitoring of gross characteristics of the phases; ready adaptability to varying blood collection requirements; and flexibility for stand-alone use or integration into automated systems.

Serum and plasma are commonly used analytical samples. If serum is desired the specimen must be permitted to clot or coagulate before further separation is attempted. Activation of this clot formation may result as a consequence of contact with the glass collection tube in which the blood was collected and can be enhanced by the addition of various clot-activating materials as described in U.S. Pat. No. 4,189,382 by Zine. If plasma is desired the specimen must have an anticoagulant mixed with it immediately after collection. For this purpose such anticoagulant materials are commonly placed in blood collection devices at the time of manufacture.

The most commonly used blood collection devices are syringes and evacuated tubes. Each is characterized by advantages and disadvantages in certain situations.

With a syringe, negative pressure and draw-volume can easily be controlled. Thus rapid rushing of blood through the cannula can be limited and hemolysis, due to shear forces on red blood cells, avoided. The volume of blood drawn can also be readily controlled by the operator, permitting use of one size of syringe for collection of a range of blood volumes. On the other hand blood collected in a syringe must usually be transferred to another tube for separation of the blood components prior to analysis. In one form this problem is overcome by providing a detachable handle for the syringe plunger and a separate closure, for the needle-end of the syringe, which may be fastened after the blood is drawn. This design provides a closed, test tube-like container and is sold under the tradename "Monovette" by W. Sarstedt, Inc. (Princeton, N.J.). However, after centrifugal separation or clotting has taken place the plasma or serum fraction remains in contact with the cellular component resulting in analyte changes if it is not promptly removed to another container.

The more popular pre-evacuated blood collection tube (such as described by Kleiner U.S. Pat. No. 2,460,641) has the following advantages: once sterilized, its interior remains sterile without additional packaging; simplicity of structure and use, in that its basic form consists of only a glass tube permanently closed at one end with a rubber stopper in the open end; and it is self-healing when blood drawing is complete and the cannula which was used to puncture the rubber stopper has been removed. A problem with the evacuated collection tube is that the uncontrolled rush of blood into the tube may result in hemolysis or collapsed veins, especially when used for collection from infants or people with fragile cells or blood vessels. Another problem is the need for a wide range of tube sizes to accommodate the need for different specimen volumes. It is usually desirable to have the tube completely filled with blood, and hence the vacuum relieved, since some gaseous or volatile constituents of the blood may otherwise diffuse into the empty volume of the tube, distorting the true concentration in the sample.

The blood plasma or serum phase is readily separated from the blood cells or clot phase by centrifugation since the specific gravities of these two phases are different. The recommended and usual practice is to centrifuge the specimen at a relative centripetal acceleration of 1000 to 1200 gravities for about 10 minutes. Various materials and devices have been described to physically separate the serum or plasma from the cellular phase, which are either activated during centrifugation or applied after separation is complete. These include gel-like compositions with densities intermediate to the phases as described, for example, in U.S. Pat. No. 4,350,593 by Kessler and U.S. Pat. Nos. 3,852,194 and 4,083,784 by Zine. Such substances, as commonly used, are sealed in the evacuated blood collection tube at the time of manufacture and will migrate to, and form a barrier at, the interface between the blood phases under the influence of the correct centrifugal force. A problem with such materials is that although they are made from substances with low chemical reactivity they nevertheless contain substances which will contaminate the serum or plasma (such as low levels of some metals used as catalysts for the formation of those compositions). Some substances which are determined by blood analysis (such as low concentrations of organic-soluble, hydrophobic drugs) can be significantly adsorbed or absorbed out of the sample by such gel-like materials, resulting in incorrect analyses. Other separators consisting of a variety of plug-like objects have been used as described, for example, in U.S. Pat. Nos. 4,492,634 by Villa-Real, 3,508,653 by Coleman, 4,417,981 by Nugent, 4,425,235 by Cornell, and 4,369,117 by White. Unfortunately, these devices are more expensive to make and insert into the preevacuated collection tube and the barriers they provide are no more reliable or effective than the simpler gel-like separation materials.

A problem with most such barriers is that they may not completely isolate the serum or plasma from the cellular phase or, in the case of the gel-like separator barriers, they may be disrupted if subjected to severe jarring such as will be encountered in shipping or mailing to testing laboratories. If this should occur, interaction of the separated phases will cause inaccurate analytical results. Moreover, prolonged contact of the blood phases with a gel-like barrier separator will increase the degree of analytical error caused by interaction between the blood and the barrier. Therefore, with most such devices it is necessary to separate the phases soon after the blood is collected and then transfer the separated plasma or serum to another container for prolonged storage or transport. Problems which then arise are that the transferred sample can become incorrectly identified and that the process of transfer exposes the user to potentially hazardous or infectious blood.

A portion of the serum or plasma may be completely isolated after centrifugation by a device which is inserted into the open end of the collection tube and permits the one-way flow of serum from the collection tube into a separate sampling container through a filter which prevents any of the fibrin from passing into the serum or plasma sample. Such devices are described, for example, in U.S. Pat. Nos. 4,464,254 by Dojki, 3,929,646 by Adler, 4,602,995 by Cassaday and are manufactured and distributed under the name of "serum/plasma filter" by W. Sarstedt, Inc. It is possible to isolate the phases of blood with such a device so as to prevent diffusion of ions or other interaction between the phases. However, their use requires additional manipulation of the collection tube, consequent exposure of the user to the blood specimen and risk of contamination of the sample. Related devices employ multiple flexible containers with provision for flow of blood fractions from the collecting blood bag into a separate reservoir (for example, U.S. Pat. Nos. 4,447,220 by Eberle and 4,322,298 by Persidsky) but these are bulky complex systems only for the separation of anticoagulated blood and are not suitable for collection and preparation of samples for routine clinical analysis.

For some analyses, such as in the area of blood banking where blood is typed and crossmatched, it is necessary to sample not only the serum or plasma but also the clot or cellular phase. Serum separator devices and methods similar to those described above have been further described in U.S. Pat. Nos. 4,046,699 by Zine and 4,326,959 by Ferrara; these devices permit ready access to both phases of the collected blood. A problem with any of these devices is that they require additional manipulation by the user and consequent greater exposure of the user to the blood specimen and risk of infection.

In some situations the use of conventional centrifuges to separate serum or plasma from the cellular component of blood specimens is undesirable because it requires a large and expensive centrifuge, best suited for separating batches of several specimens simultaneously. This operation is inefficient when the serial analyses of single samples is urgently required. Time must also be taken to properly balance the centrifuge rotor to prevent excessive vibration which may damage the machine and specimens. An apparatus such as the "Stat-Spin" axial centrifuge, developed and manufactured by Norfolk Scientific, Inc. (Norwood, Mass.), can effect this separation on a single specimen more quickly, however, the technique employed by this apparatus is limited to anticoagulated blood, collected separately in a conventional blood collection device and transferred to a specialized centrifuge chamber containing gel-like separation material. Moreover this transfer increases the hazard of contamination or loss of the sample, misidentification, and exposure of the operator to potentially infectious material in the blood. The use of an additional container increases the cost of analyzing a sample.

Similar objections and disadvantages apply to the "ACR-90" centrifuge chamber, rotor and "Airfuge" drive manufactured and sold by Spinco Division of Beckman Instruments, Inc. (Palo Alto, Calif.). This rotor is dual chambered and intended for isolation of the large lipid particles from lipemic sera. At high rotational speeds (typically greater than 90,000 rpm) the plastic chamber deforms, permitting the less dense lipid phase to migrate to a second chamber where it is trapped. Other axially spun centrifuge rotors, with a single volume often divided by vanes, are well known as "zonal rotors" and used for harvesting particles from a large volume (0.3–1.7 liters) of dilute solution such as preparations for vaccine by virologists and other such macromolecular isolates (Anderson, N. G.: Preparative zonal centrifugation. Methods of Biochemical Analysis 1967; 15: 271-310). Zonal rotors may be loaded and unloaded through a rotating seal while spinning (dynamically). A majority cannot be loaded or unloaded statically, while a few cannot be loaded or unloaded dynamically. In either case they are usually used for ultracentrifugation at rotational speeds of 20,000–60,000 rpm. Fluids are loaded by a pump and unloaded from them by displacement with air or a denser fluid pumped in during rotation. A single chamber, axially spun, centrifuge rotor with a variable volume which can be used for separation of plasma from blood was described by Brown in U.S. Pat. No. 4,530,691. This is intended for preparation of blood fractions for therapeutic use and relies upon the fractionation by centrifugation and isolation of those fractions by release of pressure exerted by a spring-loaded movable mandrel upon a flexible chamber. In this way the higher density cellular components can be taken off from the outer radius and the plasma through the center through fluid conduits while the rotor is in motion. Neither of these technologies (zonal ultracentrifugation nor centrifuge with a movable mandrel) is suitable for the fractionation of blood specimens as normally required for clinical analyses. The volumes are too large; they require the use of anti-coagulants and cannot be used with clotted whole blood; and they are not readily adapted for automated procedures.

Procedures for blood separation and analysis expose laboratory personnel to infectious agents that may be passed through contact with blood; e.g. hepatitis or acquired immune deficiency syndrome. In addition, conventional batch processing of blood specimen separation is labor-intensive and has not generally been automated whereas other processes in clinical laboratories have. Automation of blood separation can effectively isolate laboratory personnel from the dangers of blood processing while theoretically increasing the speed of the overall analytical procedure.

SUMMARY OF THE INVENTION

The present invention provides a method and apparatus for partitioning a pre-selected phase of a sample of liquid such as blood in a chamber. The method according to the invention comprises the steps of containing the sample in a tubular chamber having a pre-determined length and constant cross sectional shape, ordering the phases of the sample by rotating the chamber about its longitudinal axis, reducing the volume of the chamber in response to a separation control signal while the phases are ordered, receiving from the chamber the separated phases in order of phase, deriving information about the portion of the sample being received from the chamber, and using this information to modify the separation control signal.

Additional aspects of the method include producing a spin control signal to control the speed and duration of the rotation by modifying the spin control signal in response to information derived from the sample, and initially establishing a partial vacuum in the chamber to facilitate introducing the sample into the chamber.

The invention also provides apparatus for partitioning a pre-selected phase of a liquid such as blood according to the method, comprising: a chamber having a pre-determined initial length and a cross sectional shape which is substantially constant along its length, in which a sample of liquid is contained; a sample ordering means in which the chamber is rotated about its longitudinal axis to order the phases of the sample; a sample partitioning means for determining the portion of the sample to be partitioned; a chamber volume control means for reducing the chamber volume; and a valve means for receiving an ordered portion of the sample.

Other objects of the present invention include: providing a sample sensing means for sensing a parameter of the sample and producing a signal representative thereof; providing a means whereby the chamber volume control means is responsive to a control signal produced by the sample partitioning means; providing a means by which the sample ordering means is responsive to a signal produced by a second sample sensing means; aiding introduction of the sample into the chamber by providing apparatus in which the chamber initially contains a partial vacuum; and providing apparatus wherein the chamber includes markings which can be remotely sensed while the chamber is rotating in order to produce a chamber identification signal.

An apparatus according to the invention comprises an evacuated tubular chamber or syringe-like blood collection device which can be used in a conventional manner with available blood collection cannulae to collect a blood sample, and contains clot activation materials or anticoagulants as required, a separating means consisting of a device to rotate the evacuated tubular chamber or syringe-like device at a rotational speed and for a duration that can be adjusted with a control signal, and a means for displacing a partition within either the test tube or syringe-like blood collection device such that the separated phases of the blood sample are displaced into a containment sub-volume within the blood collection device in order of increasing density.

Advantageously, the invention provides a physical barrier between the phases of the sample, such that the separation of the phases can be maintained over a long time period and both the evacuated tubular chamber and syringe-like devices can be used in a conventional centrifuge. Additional advantages of the syringe-like blood collection device are that one size of the device can be used to collect blood samples of varying volumes, and hemolysis of the sample is reduced through control of the partial vacuum present in the blood collection device.

BRIEF DESCRIPTION OF DRAWINGS

FIG. 1 shows the preferred blood collection and separating assembly of this application being used to separate blood.

FIG. 1a illustrates the preferred blood collection and separating assembly.

FIG. 1b shows the preferred collection and separating assembly being loaded with a blood sample.

FIG. 1c shows the preferred collection and separating assembly loaded with a blood sample.

FIG. 1d shows the preferred collection and separating assembly being spun around its longitudinal axis so as to cause separation of the loaded blood sample into its denser cellular component and its less dense non-cellular component.

FIG. 1e shows the isolation of the cellular and non-cellular components of the seprated blood sample in the preferred collection and separating assembly.

FIG. 1f shows the preferred collection and separating assembly with the cellular and non-cellular components fully isolated.

FIG. 1g shows the separated non-cellular component of the blood sample being drawn from the preferred collection and separating assembly.

FIG. 2 shows the preferred collection and separating assembly separating blood sample after conventional centrifugation.

FIG. 3 shows the alternate blood sample collection and separating assembly of this application being used to separate blood.

FIG. 3a illustrates the alternate blood sample collection and separating assembly of this application.

FIG. 3b shows the alternate assembly in its expanded position.

FIG. 3c shows blood being drawn into a first chamber of the alternate collection and separating assembly.

FIG. 3d shows the alternate collection and separating assembly as it is being spun around its central axis causing radial separation of the blood sample.

FIG. 3e shows the alternate collection and separating assembly being collapsed during spinning such that the non-cellular component passes from the blood collection chamber to the serum collection chamber by way of an intermediate chamber where the presence of cells can be detected.

FIG. 3f shows cells entering the intermediate chamber of the alternate collection and separating assembly.

FIG. 3g shows the alternate collection and separating assembly stationary with blood separation complete.

DESCRIPTION OF SPECIFIC EMBODIMENTS

Figure 2E:
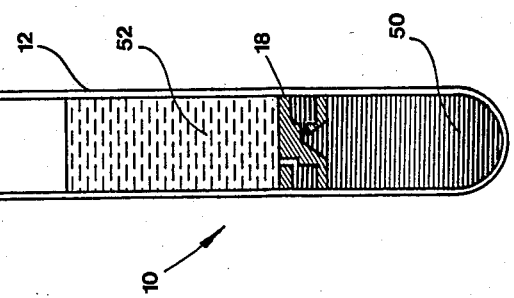
FIG. 2e shows the preferred collection and separating assembly with the cap removed to provide access to the separated non-cellular component.

Referring now to the drawings in detail, FIGS. 1 and 2 illustrate the preferred embodiment of a sample collection and separating assembly of the present invention.

The preferred sample collection and separating assembly 10 shown in FIGS. 1 and 2 consists of a tubular chamber 12 and a formed cap assembly 14.

Tubular chamber 12 is preferably constructed of glass, plastic or some other transparent or translucent and chemically inert material, has predetermined length and constant cross-sectional shape, and has a closed end and an open end shaped to receive and be adequately sealed by cap assembly 14. Tubular chamber 12 may also include non-removable machine readable markings, such as a bar code, located around the perimeter of said tubular chamber 12. Said markings allow a specific sample collection and separating assembly 10 to be uniquely identified while it is being rotated around its longitudinal axis.

Said cap assembly 14 comprises pierceable closure segment 16 and separating segment 18 attached at separable joint 20. Cap assembly 14 is so constructed to allow detachment of separating segment 18 from closure segment 16 at separable joint 20 when axial probe 22 is forced through said closure segment 16. Cap assembly 14 also forms a seal with the inside wall of tubular chamber 12 adequate to allow said chamber 12 to be pre-evacuated to aid in blood sample collection. In addition, separating segment 18 forms a second seal adequate to prevent blood cells from passing from blood sample collection chamber 24 around separating segment 18 into serum collection chamber 26 when said separating segment 18 is moved.

Said cap 14 is preferably constructed of a self-healing medical grade butyl rubber. Cast into separating segment 18 is annular intermediate chamber 28 fed by first passage 30 from axially located port 32. Said port 32 has an orifice substantially smaller in diameter than that of tubular chamber 12 and is shaped so that port 32 forms a one-way valve is achieved. As separating segment 18 is displaced axially along tubular chamber 12 pressure builds up in blood sample collection chamber 24. Port 32 will then open allowing fluid located near the longitudinal axis of tubular chamber 12 to enter intermediate chamber 28 through first passage 30. A second passage 34 then allows the fluid to pass from intermediate chamber 28 to the gap between separating segment 18 and closure segment 16 at separable joint 20. Construction of second passage 34 allows said passage 34 to function as a second one-way valve in a manner similar to that of port 32 when pressure builds up in intermediate chamber 28.

As shown in FIG. 1b, when blood drawing needle 36, one end of which is inserted in a patient's blood vessel (not shown), punctures cap assembly 14, blood sample 38 will be drawn into blood sample collection chamber 24 by said pre-established vacuum.

Removal of blood drawing needle 36, as shown in FIG. 1c, has allowed the hole in cap assembly 14 to reseal.

FIG. 1d shows sample collection and separating assembly 10 being spun around its longitudinal axis so that concentric ordering of blood into cellular component 40 and non-cellular component 42 occurs.

FIG. 1e illustrates the separation process where axial probe 22 is inserted through pierceable closure segment 16. Said closure 16 forms a seal around said axial probe 22 so that sample collection and separating assembly 10 remains hermetically sealed. Axial probe 22 rotates with sample collection and separating assembly 10, and acts as an intermediate link to transmit an axial force from non-rotating rod 44 to separating segment 18. This force causes separating segment 18 to detach from closure segment 16 along separable joint 20 and be displaced along the length of tubular chamber 12 thereby decreasing the volume of blood collection chamber 24.

During displacement of separating segment 18 the pressure increase in blood collection chamber 24 and intermediate chamber 28 causes port 32 and second passage 34 respectively to open. Fluid (first serum or plasma, later cells) then enters intermediate chamber 28 through open axially located port 32 and first passage 30. Said fluid then leaves intermediate chamber 28 by open second passage 34 and is conducted to serum collection chamber 26. Said serum collection chamber 26 is created between separating segment 18 and closure segment 16 as separation occurs along separable joint 20. An optical sensor 46 is used to detect when cellular component 40 begins to flow into intermediate chamber 28.

FIG. 1f illustrates collection and separating assembly 10 at the moment of this detection when displacement of said separating segment 18 is being stopped. Stopping said separating segment 18 allows port 32 and second passage 34 to close and effectively isolates the fluid in blood sample collection chamber 24 and intermediate chamber 28 from the fluid in serum collection chamber 26. Although in this implementation an optical method is used to detect when the interface between blood cells and serum is reached, it is clear there are a number of other criteria (i.e. differences in viscosity, density or magnetic properties) that could be used instead. As such, the use of an optical means is not meant to be a limitation of this patent.

In addition to providing a one-way valve means, the small diameter of the orifice at the terminus of axial port 32 provides an effective method of filtering fibrin from separated serum passing into intermediate chamber 28. Fibrin in blood serum can cause blood analysis machines to clog, therefore, many clinical chemistry laboratories filter all serum as a precaution. This filtration normally involves a separate manual operation involving a disposable filtering device and is accomplished after the primary separation of serum from cells. Assembly 10 allows both serum from cell and fibrin from serum separation to be accomplished with one operation.

FIG. 1g shows non-cellular component 42 being drawn from serum collection chamber 26 by cannula 48.

Preferred sample collection and separating assembly 10 can be used to separate blood in conjunction with a conventional non-axial centrifuge. This may be accomplished in either of two ways.

The first is to construct separating segment 18 of a material having a density such that when preferred assembly 10 and its sample contents are spun in a conventional non-axial centrifuge at speeds sufficient to cause separation of cellular component 50 and non-cellular component 52 of said sample, said separating segment 18 moves under centrifugal force toward the interface of said cellular and non-cellular components 50 and 52. Said separating segment 18 will come to rest before reaching said interface as shown in FIG. 2a. This method requires that said separating segment 18 be detached from said closure segment 16 prior or concurrently to the separation of said sample by conventional centrifugation.

The second is to detach said separating segment 18 from said closure segment 16 after preferred assembly 10 and its separated sample contents have been removed from a conventional centrifuge. FIG. 2b shows preferred assembly 10 and said sample contents after conventional centrifuging. The centrifuging has caused the denser cellular component 50 to separate from the lighter serum or plasma component 52 in a longitudinal density gradient increasing away from the rotational axis of the centrifuge. After removing preferred assembly 10 from the centrifuge, separating segment 18 is broken away from closure segment 16 and pushed along the length of tubular chamber 12, possibly by a device like axial probe 22, as shown in FIG. 2c.

Figure 2D:
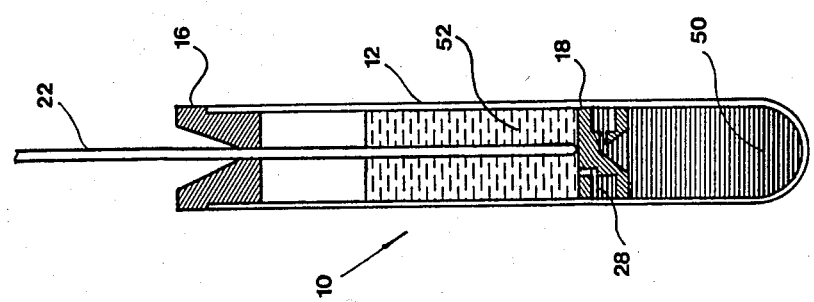
FIG. 2d shows the separating segment of the preferred collection and separating assembly after the separation of a portion of the non-cellular component of the blood sample.
Figure 2C:
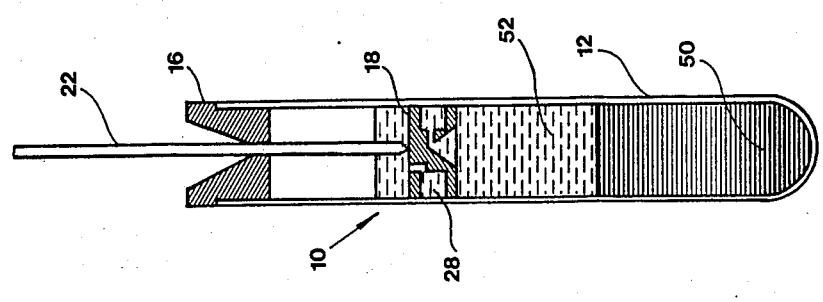
FIG. 2c shows the separating segment of the preferred collection and separating assembly being pushed through the separated blood sample.
Figure 2B:
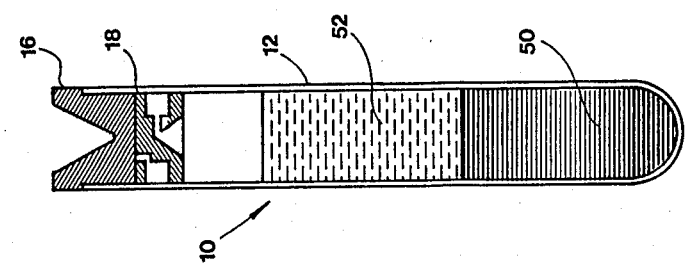
FIG. 2b shows the preferred collection and separating assembly after its loaded blood sample has been separated by conventional centrifugation and the separating segment of the preferred assembly has remained attached to the cap segment.
Figure 2A:
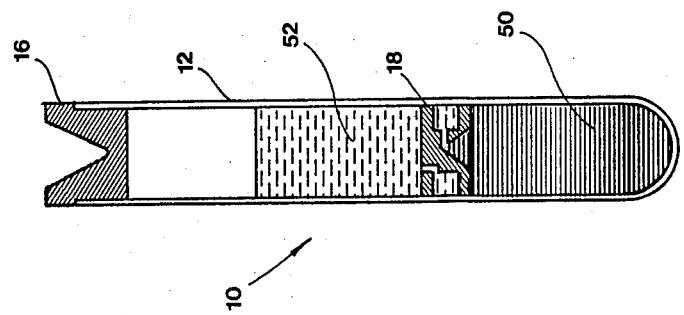
FIG. 2a shows the preferred collection and separating assembly after its loaded blood sample has been separated by conventional centrifugation and the separating segment of the preferred assembly has moved towards the serum or plasma to cell interface.

By observing when cellular component 50 begins to enter intermediate chamber 28 as shown in FIG. 2d, the operator determines when to stop the movement of said separating segment 18. Closure segment 16 can then be removed and serum or plasma component 52 decanted from said preferred assembly 10 as illustrated in FIG. 2e.

The use of an invasive device (axial probe 22 or equivalent) to cause movement of separating segment 18 may be considered a limitation on preferred assembly 10. A further limitation of preferred assembly 10 is the possibility of increased hemolysis of the sample due to the blood rushing into the pre-evacuated compartment when said sample is drawn. An alternate sample collection and separating assembly 54 (pictured in FIG. 3) allows blood to be drawn either through pre-evacuation of its blood sample collection chamber 56 or through syringe-like evacuation of said chamber 56. In addition, actuation of the separating segment of this alternate assembly 54 is accomplished non-invasively.

The device depicted in FIGS. 3a through 3g is, more specifically, a blood sample collection and separating assembly 54 consisting of lower assembly 58; blood drawing port 60; upper assembly 62; and closure 64; all of which will now be described in more detail.

Lower assembly 58, which is preferably made of glass, plastic or some other transparent or translucent and chemically inert material, has predetermined length and is tubular in cross-section with one end open to receive upper assembly 62 and the other end suitably shaped to restrain blood drawing port 60 from moving in response to either positive or negative chamber pressures. Blood drawing port 60 is preferably cast in lower assembly 58 from a self-healing medical grade butyl rubber or other suitable material. The volume between the upper and lower assemblies 62 and 58 is defined as blood sample collection chamber 56.

Upper assembly 62, which is preferably made from a transparent or translucent and chemically inert plastic, is constructed to include two pressure preferential one-way valves 66 and 68 defining an intermediate chamber 70 between them. Said upper assembly 62 also includes sealing lip 72 at the end adjacent said intermediate chamber 70. The opposite end of upper assembly 62 is constructed to receive pierceable closure 64 in such a way that closure 64 may withstand positive chamber pressures without its seal being broken, yet is still easily removed by hand. The volume between one-way valve 68 and said closure 64 is now defined as serum collection chamber 74. Upper assembly 62 may also include restraining groove 76, which is used with restraining ring 78, to lock sample collection and separating assembly 54 in an extended position.

One-way valves 66 and 68 are constructed so as to seal fluid from moving through them unless a sufficient positive pressure difference exists between blood collecting chamber 56 and serum collection chamber 74. The positioning of one-way valves 66 and 68 defines chamber 70 intermediate to blood collecting chamber 56 and serum collection chamber 74 whose volume is small by comparison to chambers 74 and 56 but whose cylindrical surface is sufficient to cause blood cells collected there to interrupt light shining through said intermediate chamber 70.

In their open position, said one-way valves 66 and 68 have orifices substantially smaller then the diameter of said lower assembly 58 and, because of this, function as coarse filters able to filter fibrin from the non-cellular component (serum or plasma) of the sample passing through said intermediate chamber 70. Assembly 54 therefore allows for both serum from cell and fibrin from serum separation to be accomplished with one operation.

Sealing lip 72 is constructed so as to provide a seal between blood collecting chamber 56 and the exterior of the tube sufficient to allow a vacuum to be created and maintained in blood sample collection chamber 56 and also to wipe blood from the sides of said collection chamber 56 when sample collection and separating assembly 54 is compressed axially. Also, said lip 72 prevents upper assembly 62 from accidentally sliding out of lower assembly 58 during normal handling of the tube but permits the removal of upper assembly 62 when access to blood sample collection chamber 56 is desired.

As shown in FIG. 3a, sample collection and separating assembly 54 is in a neutral position with all chambers at a pressure equivalent to or slightly lower than atmospheric.

FIG. 3b shows the same sample collection and separating assembly 54 as described by FIG. 3a except that upper assembly 62 has been moved relative to lower assembly 58 so as to create a vacuum in blood sample collection chamber 56. It should be noted here that one-way valves 66 and 68 are sealing so as to prevent a vacuum from occurring in either intermediate chamber 70 or serum collection chamber 74. In this position a restraining means (which could consist of restraining ring 78 inserted in groove 76) can be used to hold the vacuum in said blood sample collection chamber 56.

FIG. 3c shows blood sample 80 being introduced into blood sample collection chamber 56 with the use of tube holder 82. Affixed through the center of holder 82 is a double-ended needle 84, one end of which is inserted in a patient's blood vessel 86 while the other end pierces sample collection and separating assembly 54 through blood drawing port 60. The blood drawing procedure thus operates in a manner quite similar to a conventional blood sample collection employing an evacuated "Vacutainer TM" style test tube and either a double-ended or a "butterfly" style blood collection needle.

Upon completion of drawing blood sample 80 into blood sample collection chamber 56, and prior to axially spinning sample collection and separating assembly 54, restraining ring 78 is removed from restraining groove 76 to allow upper assembly 62 to move relative to lower assembly 58.

FIG. 3d shows blood sample collection and separating assembly 54 as it would appear after it has been spun around its axis for sufficient time at adequate speed to cause blood sample 80 to separate concentrically into denser cellular component 88 and lighter non-cellular component (serum or plasma) 90. Optical emitter 92 and detector 94 are positioned so that light is shone from emitter 92 through intermediate chamber 70 and into detector 94. It should be noted that, although this implementation uses an optical method of detecting the serum to cell interface 96, other differences between the two phases (examples given previously) could be a suitable basis for determining when this interface has been reached. As such, the use of an optical method should not be considered a limitation of this patent.

FIG. 3e shows assembly 54 while axial separation of non-cellular component 90 from cellular component 88 is being accomplished. While sample collection and separating assembly 54 continues spinning to achieve the desired radial separation, upper assembly 62 and lower assembly 58 are moved relative to each other so that upper assembly 62 passes into lower assembly 58 and blood sample collection chamber 56 is decreased in volume. This action will cause a positive pressure difference between blood sample collection chamber 56 and serum collection chamber 74 and one-way valves 66 and 68 will open. This, in turn, allows the least dense non-cellular component of the collected blood 90 to pass first into intermediate chamber 70 and then into serum collection chamber 74. Also, during the longitudinal motion between upper assembly 62 and lower assembly 58, sealing lip 72 has allowed the said pressure difference to increase and has wiped blood cells from the inside walls of lower assembly 58.

FIG. 3f shows the instant at which all non-cellular component 90 has been pushed from the center of blood sample collection chamber 56 and cellular component 88 has begun to flow into intermediate chamber 70. At this point the presence of cells 98 in intermediate chamber 70 is sensed (accomplished in our implementation through the use of optical emitter 92 and detector 94, although this is not meant to be a limitation on the patent) and compression of assembly 54 is halted. Stopping the compression causes one-way valves 66 and 68 to close thereby physically isolating non-cellular component 90 in serum collection chamber 74 and cellular component 88 in blood sample collection chamber 56 and intermediate chamber 70.

FIG. 3g shows assembly 54 after it has expanded to allow the pressures inside to equalize. The non-cellular component of blood 90 may now either be decanted from assembly 54 by removing closure 64 or drawn from the assembly by piercing said closure 64 with some type of drawing cannula. In addition, insertion of a cannula into blood collection chamber 56 through port 60 or removal of upper assembly 62 allows cellular component 88 to be conveniently drawn or decanted should said component 88 be required for analysis.

As is the case with preferred assembly 10 illustrated in FIG. 1, sample collection and separating assembly 54 can be processed in a conventional centrifuge. To accomplish this, restraining ring 78 is not removed prior to processing. Said ring 78 restrains upper assembly 62 from moving with respect to lower assembly 58 during centrifuging and is removed after the sample has been separated (longitudinally in blood sample collection chamber 56) into its cellular and non-cellular components. Upper assembly 62 is then pushed manually into lower assembly 58 until cells appear in intermediate chamber 70. Said upper assembly is then released to allow one-way valves 66 and 68 to seal serum collection chamber 74. As was the case with the axially separated sample, serum or plasma may then be removed from said serum collection chamber 74 by withdrawing or piercing closure 64 and cellular component 88 may be extracted by removing upper assembly 62.

Figure 4:
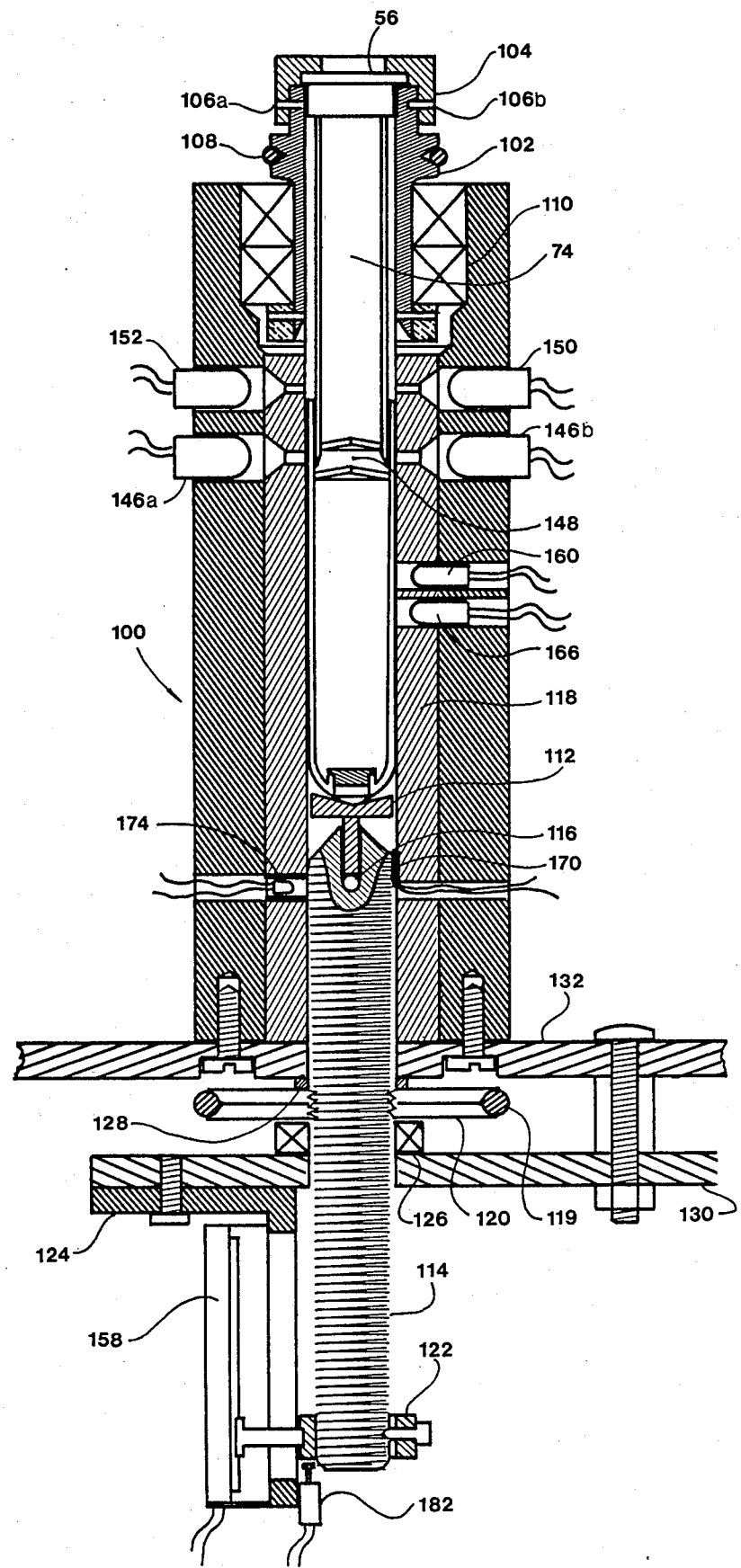
FIG. 4 is an illustration of an apparatus that accomplishes separation of a blood sample in the alternate collection and separating assembly.

FIG. 4 illustrates a device constructed to cause axial blood separation in sample collection and separating assembly 54. This device is hitherto referred to as an axial centrifuge 100.

In general, assembly 54 is clamped to rotor 102 of axial centrifuge 100 by clamp 104 engaging pins 106a and 106b and spun at high speed by rotational belt drive 108. Bearings 110 support rotor 102 and allow said rotor 102 to spin with a minimum of frictional resistance. The small mass and low frictional resistance of rotor 102 and assembly 54 allow high rotational accelerations and speeds to be achieved which can dramatically reduce the time that the sample collected in assembly 54 must be spun.

A dish-shaped live center 112, which is preferably made of "Delrin TM" or some other low friction plastic, spins in an axial hole located at the tip of lead screw 114, and supports said assembly 54 at its rounded end. A small diameter steel ball 116 provides point contact between said lead screw 114 and siid live center 112 to decrease wear and frictional heating in both components. Assembly 54 is restrained from radial motion or vibration by a loose fitting sleeve 118.

Engaging displacement belt drive 119 causes pulley 120, which has an axial hole threaded to accept the thread of lead screw 114, to rotate on said lead screw 114. As lead screw 114 is constrained against rotation by guide 122 and bracket 124, rotation of said pulley 120 relative to said lead screw 114 moves said live center 112 axially and compression of assembly 54 occurs in the process. Thrust bearings 126 and 128 and thrust plate 130 transmit the force generated by compression of air in the serum collection chamber 74 of assembly 54 to base 132.

Figure 5:
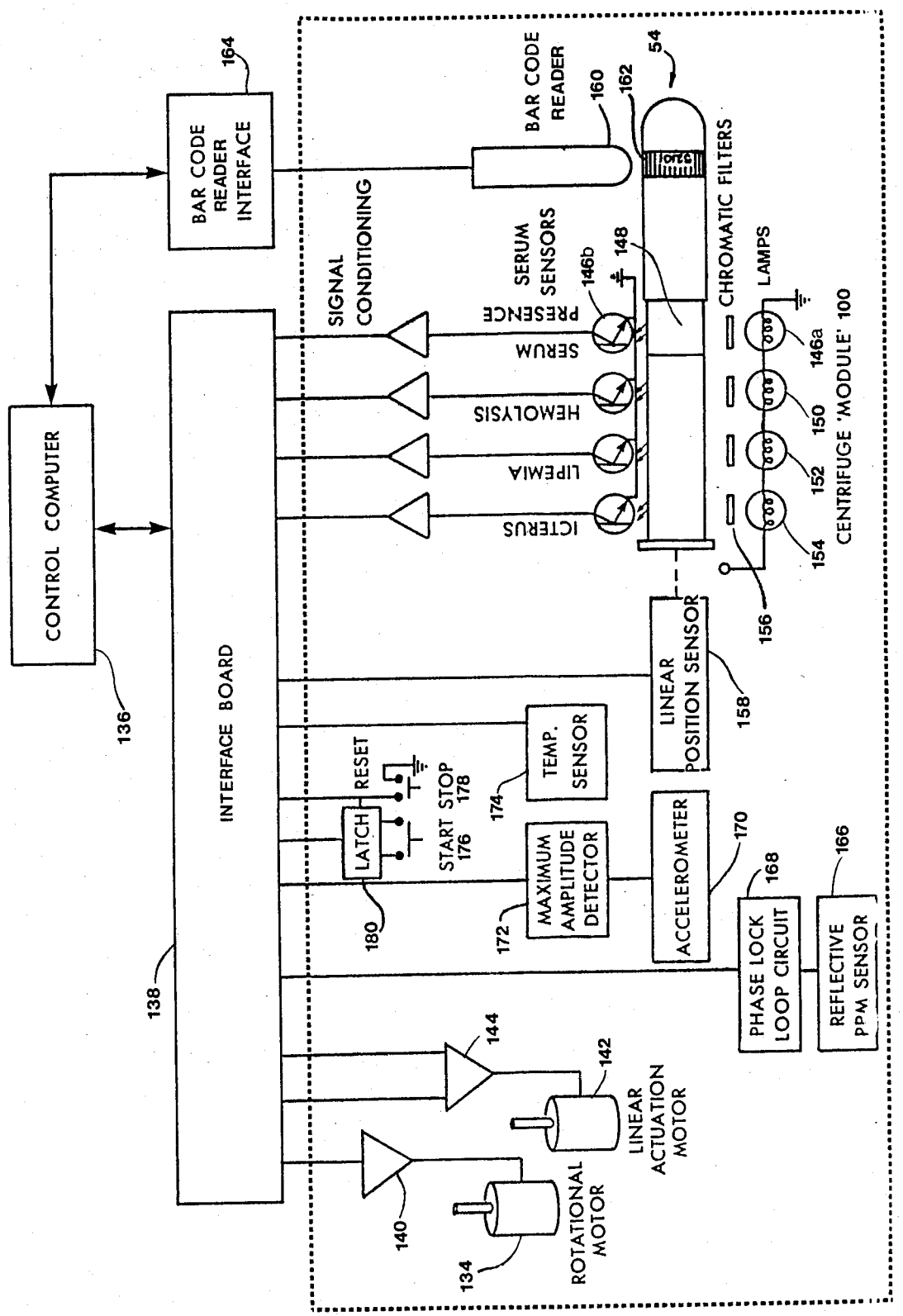
FIG. 5 is a block diagram of the sensors and control hardware of the machine of FIG. 4.

FIG. 5 is a schematic of the control and sensing circuit of axial centrifuge 100. Control of the speed of rotational motor 134 is accomplished by control computer 136, interface board 138, and rotational speed control circuit 140. Control computer 136 and interface board 138 produce a signal proportional to a set rotational speed of the tube. Rotational speed control circuit 140 causes rotational motor 134 to rotate at a speed proportional to this signal.

Control of the linear velocity of the linear actuation motor 142 is accomplished by control computer 136, interface board 138, and linear velocity control circuit 144. Control computer 136 and interface board 138 produce a signal proportional to a set linear velocity of the tube. Linear velocity control circuit 144 causes linear actuation motor 142 to advance or retract at a speed proportional to this signal.

As sample collection and separating assembly 54 undergoes rotational motion (no translation), stationary sensors mounted on axial centrifuge 100 may be used to gather information about the sample. Optical emitter and detector pair 146a and 146b are used to sense the presence of cells in intermediate chamber 148 which remains fixed axially as the lower part of assembly 54 slides over it. Three emitter and detector pairs 150, 152 and 154 use chromatic filters 156 to return a signal indicative of the color and degree of turbidity of the separated fluid as would be required to sense the presence of, for example, hemolysis, icterus, and lipemia of serum or plasma retrieved from the sample. In addition, control computer 136 uses the signals produced by optical sensor pairs 146a and 146b, 150, 152, and 154 to determine when optimal separation of the blood sample has occurred. By pulsing the compression of assembly 54 both forwards and backwards until it is determined that all serum or plasma has been separated from the blood sample, an adaptive separation method is achieved where any given sample is spun for only as long a time as it needs independent of prior results or the processing of other samples.

Linear position sensor 158 provides an accurate measurement of the amount of compression of assembly 54. When used in conjunction with emitter 146a and detector 146b, linear sensor 158 can help determine the volume of serum or plasma so far recovered by measuring the compression of assembly 54 from the time serum or plasma first begins to enter intermediate chamber 70.

The identity of said sample is determined by a bar code reader 160 reading a bar code 162 embedded or attached to the side of the tube as it spins. Bar code reader interface 164 transfers the read information to control computer 136. Given the tube identity input, control computer 136 could then access a general laboratory data-base to determine the test to be performed (including the volume of serum required) or to update the data-base for a patient if lipemia or excessive hemolysis are detected in the serum.

Several sensors are used to detect conditions of the environment of the axial centrifuge. Reflective optical sensor 166 and phase lock loop circuit 168 use bar code 162 to produce a signal proportional to the speed of rotation of the tube. The control computer 136 can use this signal to calculate the centrifugal force produced inside the tube and thus, for a given speed of rotation, determine the minimum spin time required for adequate separation of the blood sample. Accelerometer 170 with maximum amplitude detector 172 produce a signal proportional to the maximum instantaneous vibration of the axial centrifuge structure to detect gross abnormalities in operation. Temperature sensor 174 is used to monitor the temperature of centrifuge 100 and allows for observation of any frictoonal heat build-up.

Start button 176 manually initiates the separation sequence, while stop button 178 is used to manually interrupt said sequence. Latch 180 is used to hold the start line of interface board 138 at its high value and is cleared by stop button 178 resetting the start line to its low value.

Limit switch 182 is used to determine full retraction of lead screw 114.

Figure 6B:
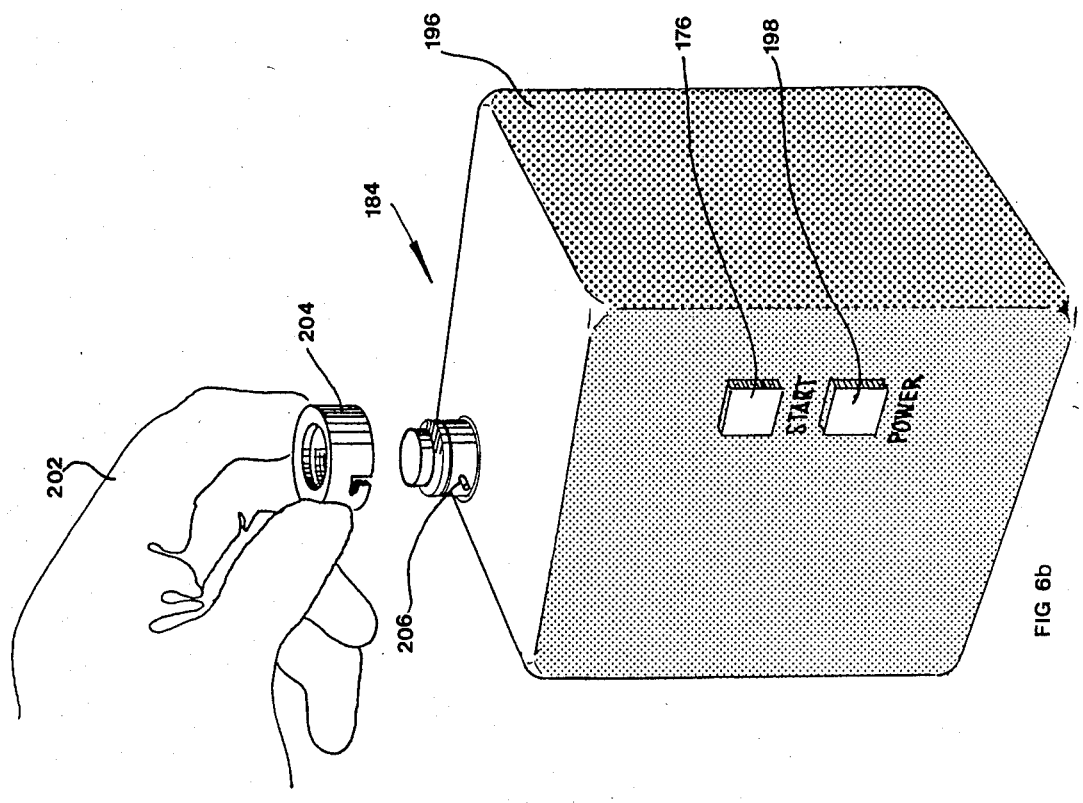
FIG. 6 illustrates the manual loading of a blood sample into the machine of FIG. 4.
Figure 6A:
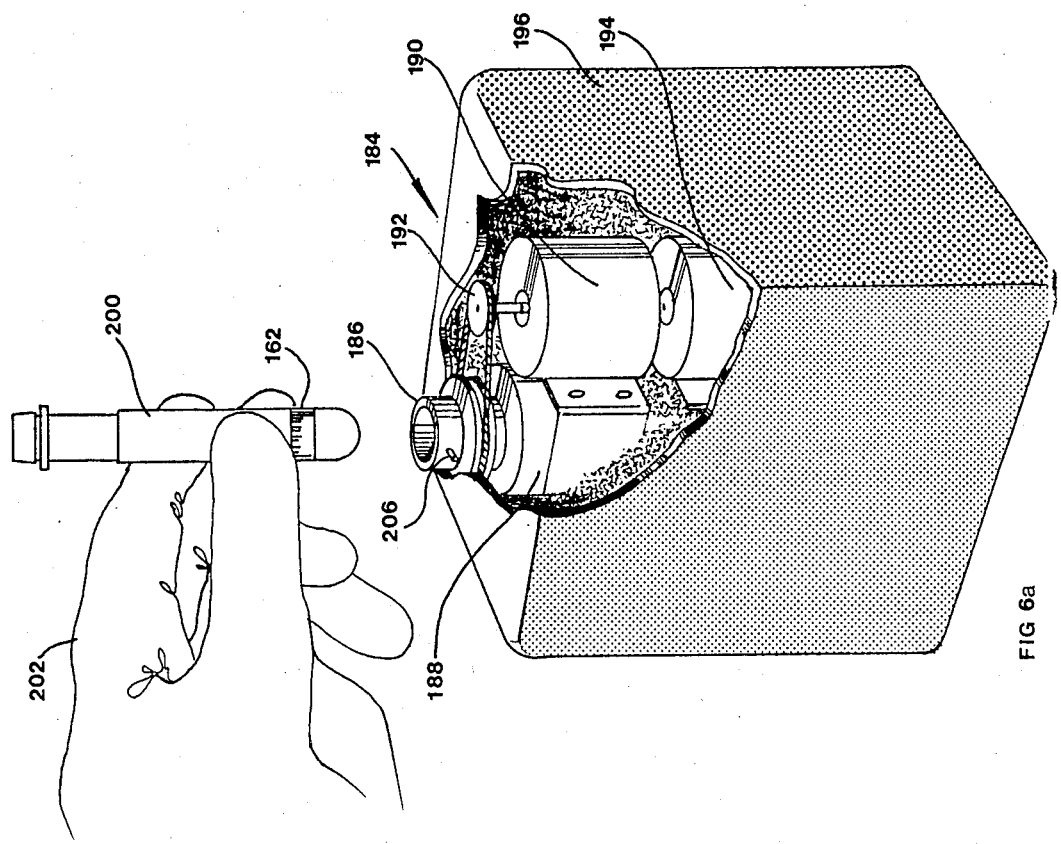

The pictorial drawings of FIGS. 6a and 6b illustrate how a single encapsulated axial centrifuge unit 184 is loaded by hand. Centrifuge unit 184 includes rotor 186 and frame 188. Rotor 186 is driven by a high speed motor 190 through a first pulley and belt drive 192. Similarly, the axial lead screw 114 is driven by a second motor 194 through a second pulley and belt drive (not shown). Centrifuge 184, drive unit and the independent control electronics are encapsulated by cover 196 so all that appears to the centrifuge user are rotor 186 and controls needed to initiate and modify the blood separation process (in the simplest form only power button 198 and process start button 176 would be required).

Blood sample 200 is loaded by a technician (or qualified other) 202 into rotor 186. Clamping cap 204 is then affixed to rotor 186 by the pressing of said cap 204 down onto said rotor 186 and, with a twist, the securing of "bayonet" style notches in said cap 204 around protruding pins 206. Blood sample 200 is inherently balanced when spinning, so no additional operations are required to balance the centrifuge module (e.g. the addition of balancing tubes).

In the simplest mode the user initiates the blood separating process by pressing start button 176. Once spinning has begun no further user involvement is required during the separation process. Any discrepancies from the expected vibration or temperature level of the sample are detected by the module which then interrupts driving power to the machine. Problems involving human error, such as failure to load sample 200, failure to clamp cap 204 on or the loading of a leaking sample are not detected by the module and must be corrected by hand after the power is turned off. In general however, the sample is spun for a preset (or adjustable) length of time at a high rotational speed in order to cause separation of the sample radially. Displacement of the lower density component from the center of the sample is then initiated and continues until the denser cellular component of the sample is detected. The displacement procedure is then stopped and high speed motor 190 is turned off.

In computer-controlled mode the separation process maybe initiated from the keyboard of the controlling computer 136 or by a program running on said controlling computer. While the sample is being spun, the identification number of the test tube is read from bar code 162 on the tube and can be displayed on the computer terminal for confirmation or stored in computer memory. In addition, this tube identification number can be used by control computer 136 to reference data about the sample in a main laboratory data base (i.e. patient's name, tests to be performed on the sample, etc.) The displacement procedure is then initiated as in the simplest mode and sensors on the centrifuge module send to the computer information on the quality (presence and extent of hemolysis, lipemia or bilirubin in the serum) and volume of the serum that has been extracted from the sample. This information may be displayed on the computer terminal or stored in memory in affiliation with information garnered from the sample's bar code. Termination of the displacement procedure can be initiated by any one of five means: by manual interruption from the keyboard; by detection of blood cells in the tube's intermediate chamber; by a serum quality reading that falls below some preset guideline; by recovery of a sufficient volume of serum to complete the required tests; or by detection of an operational malfunction. As in the simplest case termination involves the interruption of the displacement procedure and the stopping of the rotational drive.

Clamping cap 204 is then removed in the reverse manner to which it was applied. Grasping the top of sample 200, technician 202 removes said sample 200 from the module. Serum or plasma may then be extracted from said tube either by removing the closure located at the top of the tube and decanting or by piercing said closure with a cannula and drawing out serum or plasma. The remaining portion of the tube is then either discarded or stored for further tests.

Figure 7:
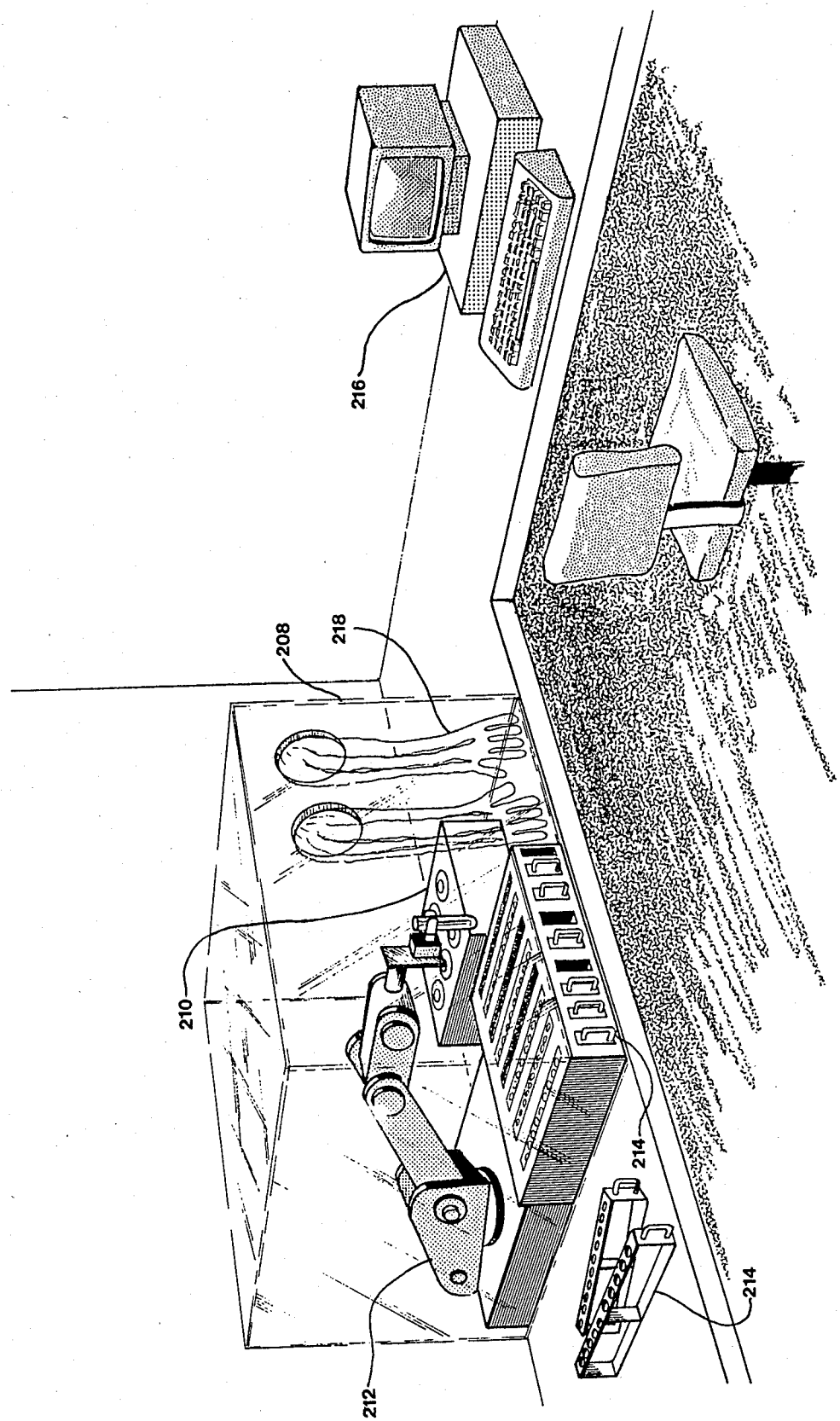
FIG. 7 is an illustration of an isolated blood separating workcell incorporating several machines as illustrated in FIG. 4.

FIG. 7 illustrates several features of the axial separation process and the centrifuge of this application as they relate to automated handling of blood samples. Isolated blood separating workcell 208 incorporates six axial centrifuges 210, robotic arm 212, buffers 214 for delivery of the preferred embodiment sample tubes into said workcell 208, and computer 216 for controlling said workcell 208 and accessing data on the samples.

Axial centrifuges 210 are truly serial processors constituting a random access machine where any one module can be accessed independent of any other module. This condition aids in optimizing the per unit service time of any sample in the workcell.

The small size of each centrifuge module facilitates the arrangement of these modules in the limited work envelope of a robotic workcell and, as the position of a sample tube does not change in space, said sample tube is easily located by said robotic arm 212 for loading and unloading.

Isolation gloves 218 are used for manual intervention in said workcell 208 thus providing the flexibility of manual manipulation while retaining the isolation of potentially hazardous blood samples or aerosols afforded by the encapsulation.

Since many changes can be made in construction of the above sample collecting and separating containers, axial centrifuge, and applications of the machine and process of this invention without departing from the scope thereof, it is intended that all matter contained in the above description or shown in the accompanying drawings shall be interpreted as illustrative and not in a limiting sense. Examples would be the addition of blood clot activators or anticoagulants to the sample containers, or the modification of the axial centrifuge to spin at a higher speed through the use of a different drive/bearing combination. Accordingly the invention is to be limited only by reference to the appended claims.

We claim:

1. A method for partitioning a pre-selected phase of a sample of liquid, comprising the steps of:
    containing in an elongated chamber having a substantially constant cross-sectional area a sample of liquid having a plurality of phases of differing densities;
    ordering the phases of the sample concentrically by rotating the chamber around its longitudinal axis;
    while the phases are ordered, reducing the volume of the chamber in response to a separation control signal by reducing the length of the chamber;
    receiving from the chamber in order of phase the portion of the volume of sample which exceeds the volume to which the chamber is reducing;
    deriving phase-separation information about the portion of the sample being received from the chamber; and
    modifying the separation control signal upon comparison of the derived information with reference information to further reduce, hold constant, or increase the volume of the chamber.

2. A method as described in claim 1 wherein the rotation of the chamber around the longitudinal axis is controllable by a spin control signal, and including the steps of:
    producing a spin control signal to control the speed and duration of rotation; and
    deriving phase-separation information from the sample and comparing the derived information to stored reference information; and
    modifying the spin control signal in response to the results of the comparison between the derived information and stored information.

3. A method for partitioning a pre-selected phase of a liquid sample, comprising the steps of:
    establishing a partial vacuum in an elongated chamber having a substantially constant cross-sectional area;
    containing in the chamber a sample of liquid having a plurality of phases;
    ordering the phases of the sample by rotating the chamber around its longitudinal axis;
    while the phases are ordered, reducing the volume of the chamber in response to a separation control signal by reducing the length of the chamber;
    receiving from the chamber in order of phase the portion of the sample volume that exceeds the volume to which the chamber is reducing;
    deriving phase-identifying information about the portion of the sample being received from the chamber; and modifying the separation control signal upon comparison of the derived information with reference information to further reduce, hold constant, or increase the volume of the chamber.

4. Apparatus for partitioning a sample of liquid having first and second phase portions of different densities, comprising:
    (a) an elongated tubular member for containing the sample; and
    (b) a phase separating element disposed within the tubular member and movable therein through the sample, the phase separating element including first and second apart-spaced valves having an intermediate chamber located therebetween, the sample passing through the intermediate chamber when the phase separating element is moved through the liquid, the first and second valves being configured to open when the phase separating element is moved through the sample and to close when the phase separating element is not moved through the sample.

5. The apparatus of claim 4 including control means for sending a first parameter of the sample in the intermediate chamber and for generating a control signal representative of the first sensed parameter, and for varying the movement of the phase separating element in response to the control signal.

6. The apparatus of claim 5 further including sample ordering means controllable for ordering the phases of the sample.

7. The apparatus of claim 6 wherein the control means further includes second sensing means for sensing a second parameter and for generating a control signal representative of the second sensed parameter, and for varying the sample ordering means in response to the second sensed parameter.

8. The apparatus of claim 6 wherein the sample ordering means orders the sample so that the first phase portion is nearer to the longitudinal axis of the tubular member than is the second phase portion.

9. The apparatus of claim 5 wherein the tubular member includes indicia attached thereto, the control means further including indicia sensing means for sensing the indicia attached to the tubular member and for generating an identification signal representative of that indicia.

* * * * *